United States Patent
Yun

(10) Patent No.: US 9,803,877 B2
(45) Date of Patent: Oct. 31, 2017

(54) BIO SENSOR AND AIR CLEANER HAVING SAME

(71) Applicant: COWAY CO., LTD, Chungcheongnam-do (KR)

(72) Inventor: Seong-Jin Yun, Seoul (KR)

(73) Assignee: COWAY CO., LTD., Chungcheongnam-do (KR)

( * ) Notice: Subject to any disclaimer, the term of this patent is extended or adjusted under 35 U.S.C. 154(b) by 0 days.

(21) Appl. No.: 15/102,936

(22) PCT Filed: Dec. 3, 2014

(86) PCT No.: PCT/KR2014/011758
§ 371 (c)(1),
(2) Date: Jun. 9, 2016

(87) PCT Pub. No.: WO2015/088174
PCT Pub. Date: Jun. 18, 2015

(65) Prior Publication Data
US 2017/0016638 A1    Jan. 19, 2017

(30) Foreign Application Priority Data

Dec. 13, 2013  (KR) .................. 10-2013-0155103
Dec. 1, 2014   (KR) .................. 10-2014-0169542

(51) Int. Cl.
*F24F 3/16*    (2006.01)
*F24F 3/14*    (2006.01)
(Continued)

(52) U.S. Cl.
CPC ..... *F24F 3/16* (2013.01); *A61L 2/26* (2013.01); *A61L 9/20* (2013.01); *F24F 3/14* (2013.01);
(Continued)

(58) Field of Classification Search
CPC ............... G01N 15/1459; G01N 21/64; G01N 2015/0046; G01N 15/0205;
(Continued)

(56) References Cited

U.S. PATENT DOCUMENTS 7,554,663 B2    6/2009  Hairston et al.
7,852,469 B1 *  12/2010 Sickenberger ......... G01N 21/53
                                                      250/288
(Continued)

FOREIGN PATENT DOCUMENTS

JP    200338163    2/2003
KR    0363865      9/2004
(Continued)

OTHER PUBLICATIONS

PCT/KR2014/011758 International Search Report, dated Feb. 24, 2015 (4 pages).

*Primary Examiner* — Kenneth J Malkowski
(74) *Attorney, Agent, or Firm* — Dority & Manning, P.A.

(57) ABSTRACT

There is provided a biosensor, which may measure the concentration of indoor bioaerosols through an optical sensing method of sensing ultraviolet light scattered by bioacrosols, and an air cleaner having the same. The biosensor includes a light irradiator and an ultraviolet light sensor detecting scattered ultraviolet light, from light irradiated by the light irradiator, reflected from bioaerosols. The biosensor may measure the concentration of indoor bioaerosols through the optical sensing method in real time, using a certain wavelength of ultraviolet light scattered by bioaerosols, and may allow the air cleaner to be operated under proper conditions based on a measured concentration of bioaerosols and a measured concentration of dust particles.

8 Claims, 2 Drawing Sheets

(51) Int. Cl.
   *A61L 9/20*       (2006.01)
   *G01N 21/53*      (2006.01)
   *G01N 15/02*      (2006.01)
   *A61L 2/26*       (2006.01)
   *G01N 15/00*      (2006.01)
   *G01N 1/22*       (2006.01)
   *G01N 15/14*      (2006.01)
   *G01N 1/24*       (2006.01)

(52) U.S. Cl.
   CPC ..... *G01N 15/0205* (2013.01); *G01N 15/1434* (2013.01); *G01N 15/1459* (2013.01); *G01N 21/53* (2013.01); *A61L 2202/14* (2013.01); *A61L 2209/111* (2013.01); *F24F 2003/1667* (2013.01); *F24F 2003/1671* (2013.01); *F24F 2003/1682* (2013.01); *G01N 1/24* (2013.01); *G01N 2001/2223* (2013.01); *G01N 2015/0046* (2013.01); *G01N 2015/0065* (2013.01); *G01N 2015/1486* (2013.01)

(58) Field of Classification Search
   CPC .......... G01N 2001/2223; G01N 1/2247; A61L 9/205; A61L 9/20; F24F 2003/1667; F24F 3/16
   See application file for complete search history.

(56) References Cited

U.S. PATENT DOCUMENTS

| 2004/0010370 | A1* | 1/2004 | Iijima | B60R 25/102 |
|   |   |   |   | 701/517 |
| 2007/0181000 | A1* | 8/2007 | Wilson | A61L 9/014 |
|   |   |   |   | 96/134 |
| 2008/0092742 | A1* | 4/2008 | Marra | B60H 3/0085 |
|   |   |   |   | 96/16 |
| 2010/0108910 | A1* | 5/2010 | Morrell | G01N 15/0205 |
|   |   |   |   | 250/459.1 |
| 2010/0263160 | A1* | 10/2010 | Oh | A47L 9/0416 |
|   |   |   |   | 15/339 |

FOREIGN PATENT DOCUMENTS

| KR | 20110009472 | 1/2011 |
| WO | WO 2009064868 | 5/2009 |

* cited by examiner

[FIG. 1]
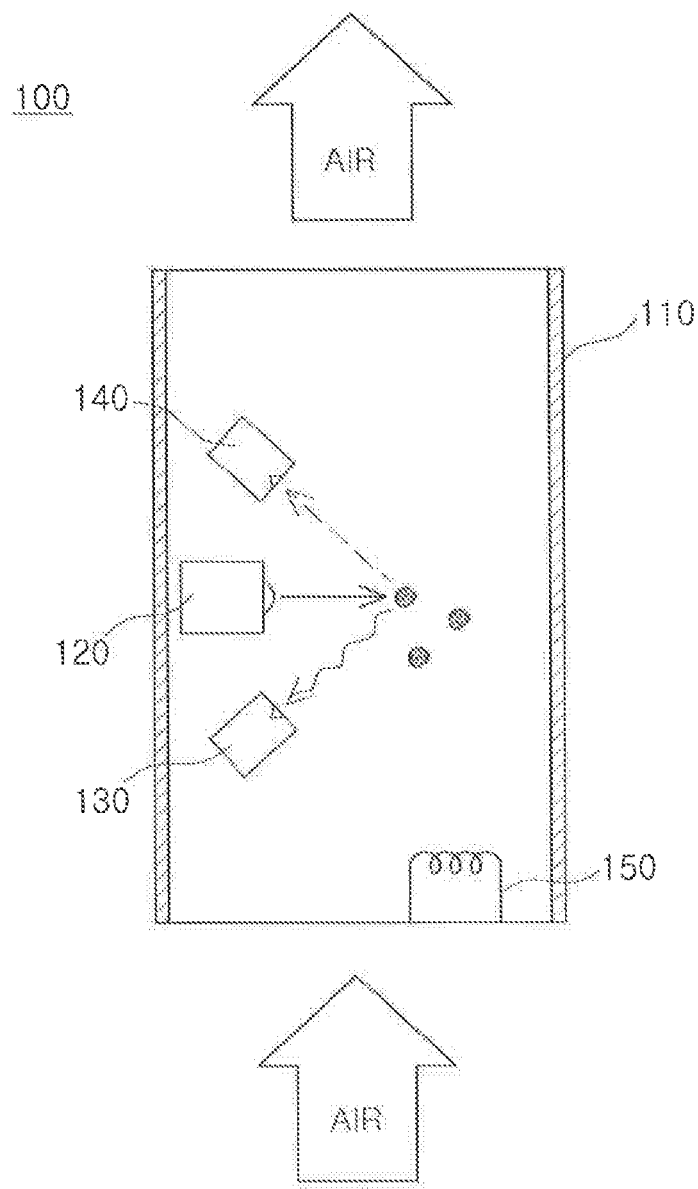

[FIG. 2]
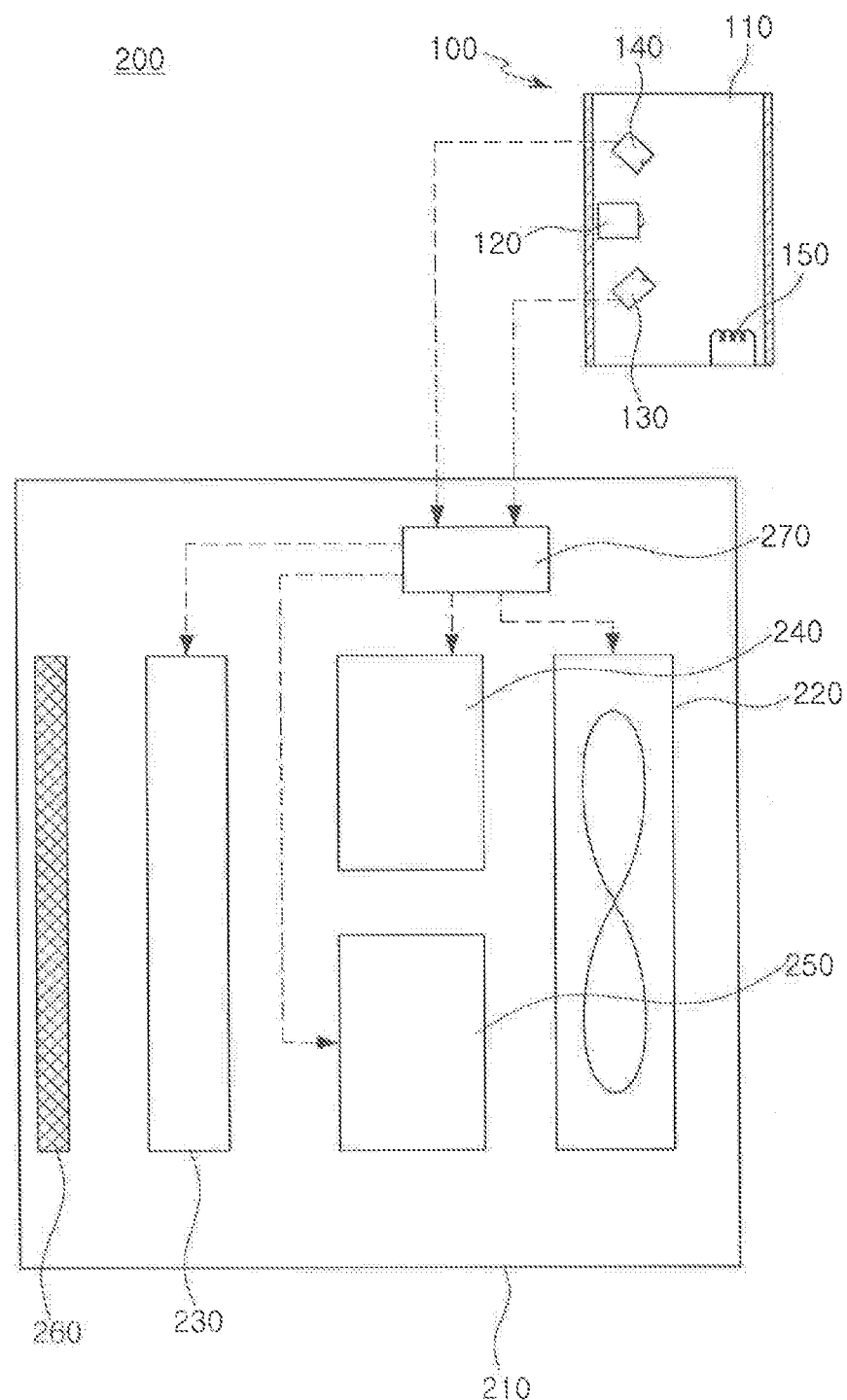

BIO SENSOR AND AIR CLEANER HAVING SAME

CROSS-REFERENCE TO RELATED APPLICATIONS

This application is the U.S. National Stage entry of International Application Number PCT/KR2014/011758 having a filing date of Dec. 3, 2014, which claims priority to Korean Patent Application Serial Number 10-2014-0169542 having a filing date of Dec. 1, 2014, and Korean Patent Application Serial Number 10-2013-0155103 having a filing date of Dec. 13, 2013.

TECHNICAL FIELD

The present disclosure relates to a biosensor and an air cleaner having the same, and more particularly, to a biosensor which may measure the concentration of bioaerosols included in the indoor air through an optical sensing method of sensing ultraviolet light scattered by bioaerosols, and an air cleaner having the same.

BACKGROUND ART

In general, air cleaners using optical sensors operate on the basis of electric signals corresponding to the concentration of dust particles.

The principle of the optical sensors is that light emitting devices irradiate light in the air flowing in a space in which the light emitting devices and detectors are provided, that the detectors detect an amount of the irradiated light scattered or reflected by dust particles included in the irradiated light, and that the concentration of the dust particles is measured.

Meanwhile, attention has recently been focused on indoor air pollution caused by bioaerosols.

However, indoor air quality measurement methods that are used to measure the concentration of bioaerosols include methods of drawing the air with air samplers to allow the drawn air to run against Petri dishes including media so that bioaerosols may stick to the media, and culturing the bioaerosols for more than a few days.

The indoor air quality measurement methods have high accuracy, but take much time to measure the concentration of bioaerosols, and therefore might not be connected to air-cleaning systems.

DISCLOSURE

Technical Problem

An aspect of the present disclosure may provide a biosensor which may measure the concentration of indoor bioaerosols in real time, and an air cleaner having the same.

Technical Solution

According to an aspect of the present disclosure, a biosensor may include: a light irradiator; and an ultraviolet light sensor detecting scattered ultraviolet light, from light irradiated by the light irradiator, reflected from bioaerosols.

The ultraviolet light sensor may convert a quantity of the detected ultraviolet light into an electrical signal.

The light may be a laser beam.

The ultraviolet light sensor may be configured to detect light having a wavelength of 300 nm to 360 nm.

The biosensor may further include a scattered light sensor detecting scattered light, from light irradiated by the light irradiator, reflected from dust particles, and converting a quantity of the detected scattered light into an electrical signal.

The biosensor may further include a passage portion including the light irradiator and the ultraviolet light sensor provided on the inside thereof, and including an air flow path, the air flow path allowing the outdoor air to flow and move therein.

The passage portion may include the air flow path configured in a vertical direction to allow the flowing outdoor air to move upwardly, and may include an air heater provided in a lower side of the passage portion to heat the outdoor air flowing in the passage portion.

According to another aspect of the present disclosure, an air cleaner may include: a housing; a blower provided in the housing and moving the air in such a manner that the outdoor air may flow in the housing and may be discharged; a sterilizer provided in the housing, and sterilizing the air flowing in the housing; a controller controlling the blower and the sterilizer; and a biosensor including a light irradiator, an ultraviolet light sensor detecting scattered ultraviolet light, from light irradiated by the light irradiator, reflected from bioaerosols, and converting a detected value into an electrical signal, and a scattered light sensor detecting scattered light, from light irradiated by the light irradiator, reflected from dust particles, and converting a detected value into an electrical signal, wherein the controller controls operations of the blower and the sterilizer based on the values detected by the ultraviolet light sensor and the scattered light sensor.

The controller may control whether to operate the sterilizer according to the presence or absence of ultraviolet light detected by the ultraviolet light sensor.

The controller may operate the sterilizer when the ultraviolet light sensor detects ultraviolet light having a wavelength of 300 nm to 360 nm.

The controller may control the blower to increase or decrease air intake according to the presence or absence of scattered light detected by the scattered light sensor.

The controller may increase air intake of the blower when the scattered light sensor detects scattered light having a wavelength of greater than 10 μm.

The controller may decrease air intake of the blower when the scattered light sensor detects scattered light having a wavelength of 10 μm or less.

The sterilizer may include at least one of an ultraviolet light generator, an ionizer, and an ozonizer.

The controller may control a humidifying operation of the humidifier and a dehumidifying operation of the dehumidifier based on the value detected by the ultraviolet light sensor.

The air cleaner may further include an air cleaning filter disposed on a flow path of the air flowing in the housing.

Advantageous Effects

According to exemplary embodiments in the present disclosure, a biosensor may measure the concentration of indoor bioaerosols through an optical sensing method in real time, using a certain wavelength of ultraviolet light scattered by bioaerosols, and may allow an air cleaner to be operated under proper conditions based on a measured concentration of bioaerosols and a measured concentration of dust particles.

DESCRIPTION OF DRAWINGS

FIG. 1 is a schematic diagram illustrating a configuration of a biosensor according to an exemplary embodiment in the present disclosure; and FIG. 2 is a schematic diagram illustrating a configuration of an air cleaner according to an exemplary embodiment in the present disclosure.

BEST MODE FOR INVENTION

The terminology used herein is for the purpose of describing particular embodiments only, and is not intended to limit the present disclosure.

In addition, the singular forms "a," "an," and "the" are intended to include the plural forms as well, unless the context clearly indicates otherwise.

Hereinafter, the exemplary embodiments of the present disclosure will be described in detail with reference to the attached drawings.

Referring first to FIG. 1, a biosensor according to an exemplary embodiment in the present disclosure will be described.

Here, FIG. 1 is a schematic diagram illustrating a configuration of the biosensor according to an exemplary embodiment in the present disclosure.

As illustrated in FIG. 1, a biosensor 100 according to an exemplary embodiment in the present disclosure may include a passage portion 110, a light irradiator 120, an ultraviolet light sensor 130, and a scattered light sensor 140, and may further include an air heater 150 provided on an entrance side of the passage portion 110.

The passage portion 110 may include an air flow path through which the outdoor air may flow and move.

The passage portion 110 may include the light irradiator 120, the ultraviolet light sensor 130, the scattered light sensor 140, and the air heater 150 provided on the inside of the passage portion 110 and described below.

According an exemplary embodiment, the passage portion 110 may be composed of a member having a pipe shape through which the air may flow to one side thereof and may be discharged to the other side thereof, but is not limited thereto.

The light irradiator 120 may irradiate light into the air flowing inside of the passage portion 110.

The light irradiator 120 may be configured to emit light that may be irradiated to bioaerosols such as dust particles and bacteria to generate scattered light.

According to an exemplary embodiment, the light irradiator 120 may be configured as a laser scanning device to irradiate a laser beam as the light.

For reference, since the laser beam is collimating light, the laser beam may have linearity that the laser beam might not spread in a traveling direction thereof, and the laser beam may thus apply high energy to very small areas of dust particles, aerosols, and bioaerosols.

Thus, as described above, the light irradiator 120 may be preferably configured to irradiate a laser beam, but is not limited thereto, and may be configured as a light source device that may emit any type of light.

The ultraviolet light sensor 130 may detect scattered ultraviolet light, from light irradiated by the light irradiator 120, reflected from bioaerosols.

For reference, when light is reflected from bioaerosols, a phenomenon that ultraviolet light is scattered in addition to a phenomenon that the light is simply refracted to scatter may occur.

Thus, the ultraviolet light sensor 130 may detect the ultraviolet light scattered by the bioaerosols to measure the concentration of the bioaerosols.

According to an exemplary embodiment, the ultraviolet light sensor 130 may be configured to have superior sensitivity to light having a wavelength of 300 nm to 360 nm in response to a wavelength of ultraviolet light scattered by bioaerosols such as *E. coli* or *substilus*, but is not limited thereto.

For reference, when light is irradiated to dust particles, aerosols, and bioaerosols, the dust particles may scatter light having a wavelength of 10 μm or more, the aerosols may scatter light having a wavelength of less than 10 μm, and the bioaerosols may scatter ultraviolet light having a wavelength of 300 nm to 360 nm.

In addition, the ultraviolet light sensor 130 may convert a detected quantity of the ultraviolet light into an electrical signal, and may transfer the electrical signal to an external element. Here, the external element may be a controller 270 provided in an air cleaner 200 according to an exemplary embodiment in the present disclosure that will be described with reference to FIG. 2.

The scattered light sensor 140 may detect scattered light, from light irradiated by the light irradiator 120, reflected from dust particles.

The scattered light sensor 140 is not particularly limited thereto, and may be configured as various types of visible light sensors publicly known.

The scattered light sensor 140 may detect light scattered by dust particles to measure the concentration of the dust particles.

The scattered light sensor 140 may convert a detected quantity of the scattered light into an electrical signal, and may transfer the electrical signal to an external element. Here, the external element may be the controller 270 provided in the air cleaner 200 according to the exemplary embodiment in the present disclosure that will be described with reference to FIG. 2.

The air heater 150 may be provided on an entrance side of the passage portion 110, for example, a side through which the air flows, to heat the air flowing in the passage portion 110.

Here, the passage portion 110 may include an air flow path formed in a vertical direction so that the flowing air may move upwardly as illustrated in FIG. 1.

Here, the air heater 150 may be disposed in a lower side of the passage portion 110 to heat the air flowing to the lower side of the passage portion 110.

The air heater 150 may heat the air flowing from the entrance side of the passage portion 110, and the air heated in the passage portion 110 may move upwardly by natural convection.

This may enable the ultraviolet light sensing unit 130 and the scattered light sensing unit 140 to measure the concentrations of bioaerosols and dust particles in a state in which the indoor air moves by natural convection without being concentrated, that is, under conditions close to an indoor environment.

As such, the biosensor 100 according to the exemplary embodiment in the present disclosure may measure the concentrations of bioaerosols and dust particles included in the indoor air in real time by the optical sensing method as described above, in particular, a method of sensing ultraviolet light scattered by bioaerosols.

Referring next to FIG. 2, an air cleaner according to an exemplary embodiment in the present disclosure will be described. Here, FIG. 2 is a schematic diagram illustrating a configuration of the air cleaner according to the exemplary embodiment in the present disclosure.

As illustrated in FIG. 2, a biosensor 200 according to an exemplary embodiment in the present disclosure may include a housing 210, a blower 220, a sterilizer 230, a controller 270, and a biosensor 100, and may further include a dehumidifier 240, a humidifier 250, and an air cleaning filter 260.

The housing 210 may form the external appearance of the air cleaner 200 according to the exemplary embodiment in the present disclosure, and may include an internal space in which the blower 220, the sterilizer 230, the controller 270, the dehumidifier 240, the humidifier 250, and the air cleaning filter 260 that will be discussed later may be provided.

In addition, although not illustrated, the housing 210 may include an air inlet provided on a side thereof and an air outlet provided on another side thereof, and may be configured to allow the air to flow in the housing 210 through the air inlet and to be externally discharged through the air outlet, through operations of the blower 220 that will be described later.

The blower 220 may be provided in the housing 210, and may allow the air to move so that the outdoor air may flow in the housing 210 and may be discharged therefrom.

According to an exemplary embodiment, the blower 220 may include a fan and a driving motor, and may be configured to adjust air volume through controlling the number of rotations of the driving motor.

The sterilizer 230 may be provided in the housing 210, and may sterilize the air flowing in the housing 210.

The sterilizer 230 is not particularly limited, and may be configured as a device that may control operations thereof through power control, and further may adjust sterilizing power.

As an example, the sterilizer 230 may include at least one of an ultraviolet light generator, an ionizer, and an ozonizer.

The controller 270 may control operations and air volume of the blower 220, and may adjust power applied to the sterilizer 230.

The controller 270 may be connected to the ultraviolet light sensing unit 130 and the scattered light sensor 140 of the biosensor 100 as described below to control the blower 220 and the sterilizer 230, based on values detected by the ultraviolet light sensing unit 130 and the scattered light sensor 140.

The biosensor 100 may include the passage portion 110, the light irradiator 120, the ultraviolet light sensor 130, the scattered light sensor 140, and the air heater 150, and may be substantially the same as the biosensor 100 described above with reference to FIG. 1.

In this case, the ultraviolet light sensor 130 and the scattered light sensor 140 may be configured to convert detected values into electrical signals and to transfer the electrical signals to the controller 270.

In more detail, the ultraviolet light sensor 130 may be configured to detect a quantity of scattered ultraviolet light reflected from bioaerosols flowing in the passage portion 110, to convert the detected quantity of the scattered ultraviolet light into an electrical signal, and to transfer the electrical signal to the controller 270.

In addition, the scattered light sensor 140 may be configured to detect a quantity of scattered light reflected from dust particles flowing in the passage portion 110, to convert the detected quantity of the scattered light into an electrical signal, and to transfer the electrical signal to the controller 270.

According to an exemplary embodiment, the biosensor 100 may be configured to be separated from the housing 210, and may also be configured to be provided outside of the housing 210.

The humidifier 250 may be provided in the housing 210, and may humidify the air flowing in the housing 210.

The humidifier 250 is not particularly limited, and may be configured as a humidifying unit of various types such as a humidifying filter type, an ultrasonic vibration type, and a heating type, but is not limited thereto.

According to an exemplary embodiment, the humidifier 250 may be composed of any one of the ultrasonic vibration type and the heating type in which a humidifying operation of the humidifier 250 may be dynamically controlled by the controller 270.

The dehumidifier 240 may be provided in the housing 210, and may dehumidify the air flowing in the housing 210.

The dehumidifier 240 is not particularly limited, and may be configured as a dehumidifying unit of various types such as a dehumidifying filter type, a refrigerating cycle type, and a Desiccant type, but is not limited thereto.

According to an exemplary embodiment, the dehumidifier 240 may be composed of any one of the refrigerating cycle type and the Desiccant type in which a dehumidifying operation of the dehumidifier 240 may be dynamically controlled by the controller 270.

The air cleaning filter 260 may be disposed on a flow path of the air flowing in the housing 210 to purify the air passing therethrough.

Meanwhile, in the air cleaner 200 according to the exemplary embodiment in the present disclosure, the controller 270 may operate the sterilizer 230 according to the presence or absence of ultraviolet light detected by the ultraviolet light sensor 130.

In more detail, in a case in which the ultraviolet light sensor 130 detects ultraviolet light, bioaerosols may be present in the indoor air. The controller 270 may receive an electrical signal from the ultraviolet light sensor 130 to operate the sterilizer 230 and the blower 220, thus sterilizing the indoor air.

According to an exemplary embodiment, the controller 270 may operate the sterilizer 230 when the ultraviolet light sensor 130 detects ultraviolet light having a wavelength of 300 nm to 360 nm. At this time, in order for the indoor air to be circulated by the air cleaner 200 according to the exemplary embodiment in the present disclosure, the controller 270 may operate the blower 220 while operating the sterilizer 230.

In addition, the controller 270 may increase or decrease air intake of the blower 220 according to the presence or absence of scattered light detected by the scattered light sensor 140.

In more detail, in a case in which the scattered light sensor 140 detects scattered light, dust particles may be present in the indoor air. The controller 270 may receive an electrical signal from the scattered light sensor 140 to increase air volume of the blower 220 so that the air cleaner 200 according to the exemplary embodiment in the present disclosure may purify the indoor air to a high level (a high air volume).

According to an exemplary embodiment, the controller 270 may increase the number of rotations of the driving motor included in the blower 220 when the scattered light sensor 140 detects scattered light having a wavelength of greater than 10 μm to increase air intake of the blower 220.

Conversely, the controller 270 may decrease air intake of the blower 220 or may stop the blower 220 when the scattered light sensor 140 detects scattered light having a wavelength of 10 μm or less.

When the ultraviolet light sensor 130 detects ultraviolet light and the scattered light sensor 140 detects scattered light, the controller 270 may operate the sterilizer 230 and may increase air volume of the blower 220 so that the indoor air may have a high level of sterilization and cleanliness.

Meanwhile, the existence of bioaerosols in the indoor air may mean that the indoor air is very humid or very dry. When the ultraviolet light sensor 130 detects a large amount of ultraviolet light, the controller 270 may control a humidifying operation of the humidifier 250 and a dehumidifying operation of the dehumidifier 240 to control indoor humidity to conditions that are unfavorable to bioaerosol growth.

For example, when the ultraviolet light sensor 130 detects ultraviolet light, the controller 270 may operate the dehumidifier 240 and the humidifier 250 so that an indoor relative humidity may be 40% to 60%.

While exemplary embodiments have been shown and described above, it will be apparent to those skilled in the art that modifications and variations could be made without departing from the scope of the present disclosure as defined by the appended claims.

The invention claimed is:

1. An air cleaner comprising:

a housing;

a blower provided in the housing and moving the air in such a manner that the outdoor air flows in the housing and is discharged;

a sterilizer provided in the housing, and sterilizing the air flowing in the housing;

a controller controlling the blower and the sterilizer; and a biosensor including a light irradiator, an ultraviolet light sensor detecting scattered ultraviolet light, from light irradiated by the light irradiator, reflected from bioaerosols, and converting a detected value into an electrical signal, and a scattered light sensor detecting scattered light, from light irradiated by the light irradiator, reflected from dust particles, and converting a detected value into an electrical signal, wherein the controller controls operations of the blower and the sterilizer based on the values detected by the ultraviolet light sensor and the scattered light sensor.

2. The air cleaner of claim 1, wherein the controller controls whether to operate the sterilizer according to the presence or absence of ultraviolet light detected by the ultraviolet light sensor.

3. The air cleaner of claim 1, wherein the controller controls the blower to increase or decrease air intake according to the presence or absence of scattered light detected by the scattered light sensor.

4. The air cleaner of claim 1, wherein the sterilizer includes at least one of an ultraviolet light generator, an ionizer, and an ozonizer.

5. The air cleaner of claim 1, further comprising:

a humidifier provided in the housing, and humidifying the air flowing in the housing; and a dehumidifier provided in the housing, and dehumidifying the air flowing in the housing, wherein the controller controls a humidifying operation of the humidifier and a dehumidifying operation of the dehumidifier based on the value detected by the ultraviolet light sensor.

6. The air cleaner of claim 1, further comprising an air cleaning filter disposed on a flow path of the air flowing in the housing.

7. The air cleaner of claim 1, wherein the biosensor further comprising a passage portion including the light irradiator and the ultraviolet light sensor provided on the inside of the passage portion, and including an air flow path, the air flow path allowing the outdoor air to flow in the inside and move.

8. The air cleaner of claim 7, wherein the passage portion includes the air flow path configured in a vertical direction to allow the flowing outdoor air to move upwardly, and includes an air heater provided in a lower side of the passage portion to heat the air flowing in the passage portion.

* * * * *